(12) United States Patent
Rossi et al.

(10) Patent No.: US 7,592,377 B2
(45) Date of Patent: Sep. 22, 2009

(54) RADIOPAQUE AND ASEPTIC MATERIAL FOR IMPRESSION-TAKING

(75) Inventors: Massimo Rossi, Grignano Polesine (IT); Francesco Callegaro, Borsea (IT); Enrico Faccio, Badia Polesine (IT)

(73) Assignee: Zhermack S.p.A., Badia Polesine (IT)

( * ) Notice: Subject to any disclaimer, the term of this patent is extended or adjusted under 35 U.S.C. 154(b) by 169 days.

(21) Appl. No.: 10/799,269

(22) Filed: Mar. 12, 2004

(65) Prior Publication Data

US 2004/0229971 A1 Nov. 18, 2004

(30) Foreign Application Priority Data

May 16, 2003 (EP) .................................. 03425317

(51) Int. Cl.
*A61C 5/02* (2006.01)
*A61C 13/007* (2006.01)
*A61K 6/083* (2006.01)
*A61K 6/10* (2006.01)

(52) U.S. Cl. ........................................ 523/109; 433/224

(58) Field of Classification Search ................. 523/109, 523/117; 433/224
See application file for complete search history.

(56) References Cited

U.S. PATENT DOCUMENTS

| | | | |
|---|---|---|---|
| 4,007,153 A | 2/1977 | Smith | |
| 4,449,938 A | 5/1984 | Pollak | |
| 4,965,295 A * | 10/1990 | Schwabe et al. | 523/109 |
| 5,106,301 A * | 4/1992 | Miyahara et al. | 433/214 |
| 5,371,162 A | 12/1994 | Konings et al. | |
| 5,403,885 A | 4/1995 | Voigt et al. | |
| 5,603,616 A * | 2/1997 | Fernandes | 433/175 |
| 5,718,586 A | 2/1998 | Barrett et al. | |
| 5,830,951 A * | 11/1998 | Fiedler | 525/478 |
| 5,852,068 A * | 12/1998 | Jada | 523/109 |
| 6,239,244 B1 | 5/2001 | Stepp et al. | |
| 6,313,190 B1 | 11/2001 | Bublewitz et al. | |
| 6,342,187 B1 * | 1/2002 | Jacob et al. | 422/186.05 |
| 2003/0036036 A1 * | 2/2003 | Porter et al. | 433/174 |
| 2004/0084812 A1 | 5/2004 | Grunwald et al. | |
| 2005/0239958 A1 * | 10/2005 | Bublewitz et al. | 524/862 |

FOREIGN PATENT DOCUMENTS

| | | |
|---|---|---|
| DE | 197 11 314 A1 | 9/1998 |
| DE | 10228421 A1 | 1/2004 |
| EP | 0 263 039 A | 4/1988 |
| EP | 0 522 341 A1 | 1/1993 |
| EP | 0 579 132 A1 | 1/1994 |
| IE | 922184 | 1/1993 |
| WO | WO 01/89588 A1 | 11/2001 |

OTHER PUBLICATIONS

GE Silicones, "LIM® 6041", at least as early as Feb. 27, 2003, pp. 1-3.
Herbert T. Shillingburg et al., "Radiopacity enhancement of an experimental vinyl polysiloxane impression material", Quintessence International, 1989, vol. 20, No. 9/1989, pp. 657-663.
Michael N. Mandikos, "Polyvinyl siloxane impression materials: An update on clinical use", Australian Dental Journal, 1998, vol. 43, No. 6, pp. 428-434.
Dow Corning, "SILASTIC® BioMedical Grade ETR Elastomers (Q7-4720, Q7-4735, Q7-4750, Q7-4765, Q7-4780) Parts A & B", Ref. No. 52-1031B-01, at least as early as Mar. 11, 2004, pp. 1-6.
Brion C. Smith, "Reconstruction of Root Morphology in Skeletonized Remains with Postmortem Dental Loss", Journal of Forensic Sciences, JFSCA, Jan. 1992, vol. 37, No. 1, pp. 176-184.
Dieter Welker et al., "Dental Materials, 6. Impression Materials [53-61], 6.1.2. Elastomers", Ullmann's Encyclopedia of Industrial Chemistry,*DOI*: 10.1002/14356007.a08_251, Article Online Posting Date: Jun. 15, 2000, p. 1.

* cited by examiner

*Primary Examiner*—Tae H Yoon
(74) *Attorney, Agent, or Firm*—Pearne & Gordon LLP (57) ABSTRACT

The present invention relates to a radiopaque and aseptic material for impression-taking. Moreover, the present invention relates to the use of said material in implantodontics.

14 Claims, 5 Drawing Sheets

Fig.(1) Aluminium;
from left 0.2-0.11-0.6mm

Fig.(2) Comparative example 1;
from left 0.05-0.1-0.2mm

Fig.(3) Example 2
from left 0.2-0.1-0.05mm

Fig.(4) Example 3
from left 0.2-0.1-0.05mm

Fig.(5) Example 4;
from left 0.2-0.1-0.05mm

Fig.(6) Example 5;
from left 0.2-0.1-0.05mm

Fig.(7) Example 6
from left 0.2-0.1-0.05mm

Fig(8) Example 7;
from left 0.2-0.1-0.05mm

Fig. (9) Example 8
from left 0.2-0.1-0.05mm

Fig. (10) Example 9;
from left 0.05-0.1-0.2mm

RADIOPAQUE AND ASEPTIC MATERIAL FOR IMPRESSION-TAKING

The present invention relates to a radiopaque and aseptic material for impression-taking. Moreover, the present invention relates to the use of said material in implantodontics.

It is known that implantation surgery aims at introducing an intraosseous implant in a convenient position and angle so as to be used as denture abutment.

It is further known that in implantodontics the term "impression-taking" refers to the detection of the three-dimensional position of the implant (fixture). There are various implantation techniques, which can be summarized into five possible options, three of which concern fixed dentures and the other two removable dentures.

The techniques concerning fixed prostheses can replace partial or complete dentures and can be both screwed and cemented.

It is known that there are on the market several implants, which can be variously classified. The most logical distinctions concern the interface implant/abutment, the shape of the implant and the contact surface bone/implant.

Furthermore, it is also known about several implantation techniques, among which a specific technique is chosen according to the situation.

The main techniques for impression-taking in implantology basically differ in the way in which the transfer is secured into the impression. In the indirect method the copying transfer is introduced into the impression after impression-taking and its analogous element is secured to it, whereas in the direct technique the transfer becomes an integral part of the impression.

Conversely, quite an important technique requires the impression to be taken immediately after the introduction of the implant. Said technique is currently known as "immediate loading".

As is known, the technique of immediate loading aims at giving the patient an immediate denture solution by means of a temporary prosthesis anchored onto the implants.

Analyses carried out with test groups have shown that it is possible to load implants immediately after introducing the implant by means of dentures connecting the implants stiffly one to the other. The percentage of success is above 85%.

Immediate loading can be used in the following cases:
complicatedly edentulous mandibles with overdenture on implants;
fixed denture prosthesis in the completely edentulous mandible;
fixed denture prosthesis in the edentulous maxilla;
single bridges and crowns.

Immediate implant loading requires, beyond the biocompatibility that is necessary for any implantation technique, the possibility to obtain a high stability of said implants.

Implantation sites are prepared by following the specifications suggested by implant manufacturers.

It is known that before grafting the implant deep incisions of the gingiva as far as the bone are carried out.

The mucosa should be removed from the periosteum and the implantation site is prepared by means of particular rotary instruments. Then, after marking implant position, a pilot hole is made and, by alternating burs with increasing diameters, the seat where the implant will be grafted is defined. Once the implantation site is ready, the implant is screwed thereon. Eventually, the area is sprayed with a saline solution so as to remove debris and bone fragments, then the flaps of the soft tissues are sutured.

In implantology a potential cause of prosthetic mistakes is an erroneous impression-taking technique and unsuitable materials used to this purpose.

Therefore, there is the need for suitable materials for impression-taking having specific properties so as to be used in implantology.

A specific material for impression-taking for implantology should therefore ensure an accurate and unchangeable positioning of the transfer and thus of its analogous element in the chalk cast, so as to avoid mistakes due to rotations and misalignments.

The properties of a material for impression-taking that best ensure these features are:
dimensional shrinkage, recovering from deformation and stiffness.

Beyond being stiff the material should be elastic and anyhow non-deformable.

Since the highest stresses occur during impression removal, all deformations should be within the original size and the material should undergo no yields but a breaking so that most of the impression keeps its integrity.

The small extension further means low elasticity and therefore stiffness. The material, however, should be sufficiently elastic so as to be easily removed from the patient's mouth.

Furthermore, since impression-trays—also perforated—are used in implantology, it is necessary to use a material for impression-taking having a manifest non-Newtonian rheologic behavior (shear thinning), because the use of perforated impression-trays in the direct technique requires that the material for impression-taking has such a fluidity as to reproduce details and, at the same time, not too a high a fluidity, otherwise it would get out of the opening used to let transfers out.

Therefore, there is the need for suitable materials for impression-taking having specific properties so as to be used in implantology.

Among the mistakes provided for in post-surgical records, one that can lead to implant failure is the presence of possible residues of material for impression-taking, which could be trapped in the soft tissues within the wound.

Consequences thereof are a possible perimplant inflammation and infection.

As a matter of fact, in case of gingival inflammation we can see a higher incidence of infections of perimplant sites with respect to pericoronal sites. Under these circumstances inflammation is more serious and the inflammatory process goes deeper with a faster development around implants with respect to natural teeth.

Residues of material for impression-taking result in precise surgical complications, which can be classifies as post-implantation complications or biological complications.

In the presence of active infections (as in the case of bleeding or swelling) it is necessary to carry out a surgical operation for cleaning the site.

Therefore, there is still the need for suitable materials for impression-taking having specific properties so as to be used in implantology.

Thus, the detection of possible residues or fragments of material for impression-taking trapped in the soft tissues within the wound can be carried out with a dental arch radiography or an intra-oral radiography.

Radiographies are generally carried out immediately after implant graft or, in case of immediate loading, about 10 days after the operation.

Therefore, there is once again the need for suitable materials for impression-taking to be used in implantology in order to prevent precociously possible postsurgical complications.

The formation of fragments can take place above all in the case of impressions in partial implants comprising undercuts and narrow inter-dental gaps.

In practice, at the state of the art there is no material for impression-taking for implantology that can prevent possible post-surgical complications by identifying residues or fragments of material for impression-taking left in the soft tissues within the wound.

An aim of the present invention is to carry out a radiopaque material for impression-taking.

Another aim of the present invention is to carry out a sterile and aseptic material for impression-taking without pathogenic agents (germs, microorganisms, viruses and other forms that are dangerous for the organism), which does not generate or develop pathogenic agents.

A further aim of the present invention-is to carry out a material for impression-taking that is biocompatible with tissues.

An additional aim of the present invention is to carry out a material for impression-taking with rheologic and mechanical properties that are specific for use (as material for impression-taking) in implantodontics.

These and other aims that will be evident from the following detailed description have been achieved by the Applicant, who has carried out a material for impression-taking having specific properties so as to enable its use in implantodontics.

A first object of the present invention is a radiopaque and sterile material for impression-taking for implantology, whose characteristics are listed in the appended claim.

Another object of the present invention is a process for preparing a radiopaque and sterile material for impression-taking for implantology, whose characteristics are listed in the appended claim.

A further object of the present invention is the use of a radiopaque and sterile material for impression taking for implantology, whose characteristics are listed in the appended claim.

Further preferred non-limiting embodiments of the present invention are listed in the appended dependent claims.

BRIEF DESCRIPTION OF THE DRAWINGS

FIG. 1 shows results and data as discussed in Example 1.
FIG. 2 shows results and data as discussed in Example 1.
FIG. 3 shows results and data as discussed in Example 2.
FIG. 4 shows results and data as discussed in Example 3.
FIG. 5 shows results and data as discussed in Example 4.
FIG. 6 shows results and data as discussed in Example 5.
FIG. 7 shows results and data as discussed in Example 6.
FIG. 8 shows results and data as discussed in Example 7.
FIG. 9 shows results and data as discussed in Example 8.
FIG. 10 shows results and data as discussed in Example 9.

The radiopaque and sterile material for impression-taking according to the present invention comprises an addition silicone or a mixture of addition silicones in variable ratios one to the other according to the properties to be obtained for the material for impression-taking.

Addition silicones are biocompatible with tissues. Indeed, it is generally known (K. J. Anusavice et al. *Phillips' Science of Dental Materials X edition*, 1996, page 147, W. B. Saunders Company) that polyethers have generated the highest cell citotoxicity and the smallest number of vital cells after several expositions. Contrarily to what could be expected due to their content of lead oxide, polysulfurs have the lowest citotoxicity but, due to their organoleptic properties, are not suitable for this use. Though silicones are biologically inert, it should be admitted that condensation silicones are not wholly neutral towards cell tissues since they contain tin compounds.

Addition silicones are generally bi-component, the single components, i.e. base (B) and catalyst (A), are kept separately. Component B and component A and other components described below, if present, are mixed together short before use according to the teachings known to the person skilled in the art, according to the properties to be obtained for the material.

For instance, their mixing ratio can be of 1:10 to 10:1, preferably 1:1. As an alternative, it can be 5:1, 2:1, 4:1 or 10:1 or conversely.

The mixing operation can be carried out manually by taking the material from a tube or a cartridge equipped with a static mixer, or alternatively by means of an automatic extruder/mixer.

Components A and B consist of diorganopolysiloxanes having triorganosiloxy terminal groups in which one out of the three radical groups is a vinyl group.

Polymers of this kind preferably have the following formula (I):

$$CH_2=CH-(-SiR^1R^2O)_m-SiR^1R^2CH=CH_2 \qquad (I)$$

where $R^1$ and $R^2$ are a substituted or un-substituted monovalent hydrocarbon radical.

$R^1$ and $R^2$ can comprise double bonds.

Examples of groups $R^1$ and $R^2$ are methyl, ethyl, phenyl, vinyl or 3,3,3-trifluoropropyl radical.

The preferred radical is methyl, which can be present with other radicals.

The value of integer m is such that the viscosity of the polymer at 23° C. is between 50 cP and 1,000,000 cP. Preferred viscosities are of 200-100,000 cP.

Silicone oils with different viscosities without vinyl groups can be present as plasticizers.

In particular, component A further comprises a hydrosilylation catalyst.

Said catalyst can be chloroplatinic acid or a Pt siloxane complex.

As an alternative said catalyst can be a metal such as Rh or Pd.

The content of metallic platinum is between 5 and 500 ppm, preferably of about 100 ppm.

Component (B) further comprises a reticulating agent. Said reticulating agent is an organopolysiloxane containing at least three silicon atoms Si bonded to a hydrogen atom pro molecule. The viscosity of the reticulating agent is between 5 and 1000 cP; preferably it is between 15 and 300 cP.

The content of SiH in component B is between 0.2 and 10 millimoles/g; preferably it is between 1.5 and 3 millimoles/g.

The total content of SiH in component B should be such as to ensure the complete reaction of all vinyls present in component A and B and, furthermore, the reticulating agent can also be present in slight excess. Preferably, component A and B can comprise linear or cyclic polysiloxanes containing a high concentration of vinyls. The presence of said linear or cyclic polysiloxanes containing a high concentration of vinyls has the function of adjusting the reactivity of platinum present in component A.

Other substances that can be present both in A and B are pigments and colorants, aromatic substances, surfactant agents such as polysiloxane-polyether copolymers or alkyl phenol ethoxylate.

Another important components is the filler, which can be chosen among: extending fillers conferring filling, sliding and appearance properties; and reinforcing fillers with reinforcing function.

Whereas the first ones, i.e. extending fillers, are mineral fillers with BET surface below 50 m$^2$/g such as for instance quartz, calcium carbonate, infusorial earth, iron oxide, aluminum silicates and alumina, the second ones, i.e. reinforcing fillers, consist of fumed silica or precipitated silica with quite high BET surface and generally silanized.

All the components referred to above should be combined together in a specific way so as to carry out a material for impression-taking, comprising a bicomponent silicone to be reticulated by addition, having the necessary rheologic, mechanical, biocompatibility and sterility properties so as to be validly used in implantology.

Given the great number of clinical situations, rheology and fluidity properties cannot be obtained from one material, but all problems and various techniques can be solved with a combination of materials with different viscosities.

Furthermore, the material for impression-taking according to the present invention should also be radiopaque.

Advantageously, in order to obtain said radio-opacity high density insoluble fillers are used.

In practice, the insolubility and therefore biocompatibility of said fillers should be such as to prevent their transport into tissues.

U.S. Pat. No. 4,584,326 and U.S. Pat. No. 4,579,879 use as radiopaque substances plasticizers based on diiodobenzoates and tetralodobenzoates. Said products are inadmissible due to the simple way in which they can be released by the material for impression-taking and then conveyed into the organism.

A very important feature to be considered in the choice of the radiopaque substance is the compatibility with addition silicones and the compatibility with cell tissues.

The concentration of said insoluble fillers should be such as to enable a good shielding in the exposition conditions that can normally be obtained in a dental practice, with low thicknesses and with a sufficient contrast towards soft tissues, bone tissues and dentine.

The concentration is of 10% to 70% by weight, with respect to the total weight of the material for impression-taking.

A concentration below 10% does not give a good shielding effect.

Alternatively, a concentration above 70% gives unwanted viscosity values, which are at the same time such as to make the material for impression-taking unsuitable for use in implantodontics.

Advantageously, the concentration of said insoluble fillers is of 20 to 60% by weight.

Among insoluble fillers finely divided metals can be used, such as zinc, tungsten, silver, ytterbium, yttrium, gadolinium, zirconium, strontium, tantalum, niobium, molybdenum, lanthanum, powders obtained from alloys of said metals; their oxides such as yttrium oxide, bismuth oxide, ytterbium oxide, tungsten oxide, niobium oxide, tantalum oxide, molybdenum oxide, zirconium oxide; their sulfates such as barium sulfate and strontium sulfate; their carbonates such as bismuth oxycarbonate, strontium carbonate; other compounds such as bismuth oxychloride, calcium tungstate, tungsten carbide, tungsten carbide, molybdenum carbide, niobium carbide, tantalum carbide and zirconium carbide.

Said insoluble fillers are chosen among white substances that are easy to be found, such as for instance: barium sulfate, zirconium oxide, bismuth carbonate, bismuth oxide, bismuth oxychloride and tungsten oxide.

The advantageous properties of the material for impression-taking according to the present invention are: balance between elasticity and stiffness, fluidity and viscosity suitable to the use, biocompatibility, a color contrasting with the environment of the oral cavity (so as to simplify visual identification) and radio-opacity.

Another important property in case of use with open wounds is the sterility of the material used and of the accessories enabling application. The sterilization of the materials can be carried out by heating or with radiations.

A sterilization carried out by boiling at 100° C. for 30 minutes enables to eliminate pathogenic microbes and bacteria except for some endospores.

A sterilization carried out by autoclaving at 121° C. for 15 minutes allows to eliminate also endospores.

A sterilization carried out in dry conditions at 160° C. for two hours, or at 170° C. for one hour could give rise to problems for the packages made of plastic that are generally used.

A system enabling sterilization within finished packages is the sterilization with gamma rays with a ray dose between 1.5 and 4.5 kGray, which kills most of pathogenic bacteria. Doses between 10 and 45 kGray deactivate spores and viruses but can damage the material for impression-taking. The radiation dose should therefore be such as to reduce bacterial charge, penetrating into the whole material, without causing physical damages to the product and/or altering its organoleptic properties.

Other techniques, although not so widespread, use electron beams, which have a low penetration power, and X rays.

Therefore, the material for impression-taking can undergo a sterilizing process.

Advantageously, the material according to the present invention enables to identify possible fragments, unintentionally incorporated into soft tissues, by examining radiographies carried out after the implantation in order to verify its correctness. Said fragments do not have a definite thickness and can also be very thin. That is why the search for a radio-opacifier has focused onto those that are more efficient at low thicknesses. Thicknesses up to 50 μm have been taken into consideration.

An embodiment of the present invention relates to a process for preparing the material comprising a step in which the insoluble radio-opacifying filler is added to component A and/or B and said components are then mixed one to the other short before use according to the teachings known to the expert skilled in the art. Process variables are known to the technician, who can apply them according to the properties of the material without altering the required performances.

EXAMPLES

The following examples are merely indicative and illustrative and are not limiting.

According to ISO 4049 standard radio-opacity comparison has been carried out with aluminum strips having a thickness of 0.20-0.11-0.06 mm. A digital appliance Planmeca model Prostyle Intra for intra-oral radiographies, equipped with tube RX Toshiba model D071/SB, has been preferred to a traditional radiographic appliance. Exposition conditions were of 66 KV, 8 mA and 0.03 s at a distance of 200 mm. A glass plate has been placed under the sensor. The images thus obtained have been processed with a computer using Adobe Photoshop.

The lighter color having a greater contrast with respect to the background corresponds to a higher radioopacity.

The various components can be mixed with a planetary mixer equipped with impellers having size and shape suited to the viscosities of the products to be obtained.

Once components A and B have been prepared, they are manually mixed or placed in a cartridge and then mixed with a static mixer. The strips having different thickness are obtained by means of a hydraulic press and molds with known thickness.

Percentages are to be regarded as percentages by weight. The platinum catalyst is used as 1% solution in silicone polymer.

Example 1

Component A Comprises the Following:
polydimethylsiloxane 1000 cP 12%, polydimethylsiloxane 20000 cP 9%, micronized quartz 15%, aluminum silicate 17.3%, soda glass powder 46%, platinum catalyst 0.7%, for a total 100% of component A.

Component B Comprises the Following:
polydimethylsiloxane 1000 cP 12%, polydimethylsiloxane 20000 cP 8.3%, micronized quartz 26.7%, aluminum silicate 5%, soda glass powder 45%, reticulating agent 3%, for a total 100% of component B.

The present example has a comparative aim and is intended to show that despite the high content of fillers, the strips of set product have a lower shielding effect than aluminum strips having the same thickness FIG. 1 and FIG. 2.

Example 2

Component A Comprises the Following:
polydimethylsiloxane 200 cP 9%, polydimethylsiloxane 2000 cP 13.5%, polydimethylsiloxane 100000 cP 4.6%, polydimethylsiloxane 20000 9%, silanized fumed silica 4%, micronized quartz 13%, soda glass powder 35%, aluminum silicate 11.2%, platinum catalyst 0.7%.

Component B Comprises the Following:
polydimethylsiloxane 200 cP 4.2%, polydimethylsiloxane 2000 cP 8.6%, polydimethylsiloxane 20000 7%, reticulating agent 9%, silanized fumed silica 3%, micronized quartz 19%, soda glass powder 44.2%, micronized silver 5%

The introduction of too small amounts of metal powders with high density (2.5% on the vulcanized product) does not result in a sufficient shielding, FIG. 3. The concentration increase would lead to unwanted higher costs.

Example 3

Component A Comprises the Following:
polydimethylsiloxane 200 cP 9%, polydimethylsiloxane 2000 cP 13.5%, polydimethylsiloxane 100000 cP 4.6%, polydimethylsiloxane 20000 9%, silanized fumed silica 4%, micronized quartz 13%, soda glass powder 35%, aluminum silicate 11.2%, platinum catalyst 0.7%.

Component B Comprises the Following:
polydimethylsiloxane 200 cP 4%, polydimethylsiloxane 2000 cP 8.2%, polydimethylsiloxane 20000 6.4%, reticulating agent 8.5%, silanized fumed silica 2.85%, micronized quartz 18%, soda glass powder 42.05%, bismuth oxychloride 10%

The introduction of compounds with high atomic weight in small concentrations enables to obtain a scarcely sufficient radio-opacity, FIG. 4.

Example 4

Component A Comprises the Following:
polydimethylsiloxane 200 cP 9%, polydimethylsiloxane 2000 cP 11.5%, polydimethylsiloxane 100000 cP 4.2%, polydimethylsiloxane 20000 9%, silanized fumed silica 4%, soda glass powder 32%, aluminum silicate 9.5%, bismuth subcarbonate 20%, platinum catalyst 0.8%.

Component B Comprises the Following:
polydimethylsiloxane. 200 cP 4.2%, polydimethylsiloxane 2000 cP 8.8%, polydimethylsiloxane 20000 8%, reticulating agent 9%, silanized fumed silica 3%, soda glass powder 47%, bismuth subcarbonate 20%

The radio-opacity level is better than aluminum, FIG. 5.

Example 5

Component A Comprises the Following:
polydimethylsiloxane 200 cP 9%, polydimethylsiloxane 2000 cP 11.5%, polydimethylsiloxane 100000 cP 4.2%, polydimethylsiloxane 20000 9%, silanized fumed silica 4%, soda glass powder 32%, aluminum silicate 9.5%, bismuth trioxide 20%, platinum catalyst 0.8%.

Component B Comprises the Following:
polydimethylsiloxane 200 cP 4.2%, polydimethylsiloxane 2000 cP 8.8%, polydimethylsiloxane 20000 8%, reticulating agent 9%, silanized fumed silica 3%, soda glass powder 47%, bismuth trioxide 20%

The radio-opacity level is better than aluminum, FIG. 6.

Example 6

Component A Comprises the Following:
polydimethylsiloxane 1000 cP 12.2%, polydimethylsiloxane 20000 cP 7.8%, micronized quartz 6.4%, aluminum silicate 17.3%, soda glass powder 45.8%, barium sulfate 10%, platinum catalyst 0.5%.

Component B Comprises the Following:
polydimethylsiloxane 1000 cP 11.5%, polydimethylsiloxane 20000 cP 8.3%, micronized quartz 16.3%, aluminum silicate 5.4%, soda glass powder 45.5%, barium sulfate 10%, reticulating agent 3%.

FIG. 7 shows the shielding effect.

Example 7

Component A Comprises the Following:
polydimethylsiloxane 200 cP 9%, polydimethylsiloxane 2000 cP 13.5%, polydimethylsiloxane 100000 cP 4.6%, polydimethylsiloxane 20000 9%, silanized fumed silica 4%, micronized quartz 13%, soda glass powder 35%, aluminum silicate 11.2%, platinum catalyst 0.7%.

Component B Comprises the Following:
polydimethylsiloxane 200 cP 4%, polydimethylsiloxane 2000 cP 8.2%, polydimethylsiloxane 20000 6.4%, reticulating agent 8.5%, silanized fumed silica 2.85%, micronized quartz 18%, soda glass powder 42.05%, tungsten oxide 10%

A 5% level of radio-opacifier is not sufficient to confer a good shielding, FIG. 8. The result is lower than a corresponding concentration of Bi oxychloride.

Example 8

Component A Comprises the Following:
polydimethylsiloxane 200 cP 9%, polydimethylsiloxane 2000 cP 13.5%, polydimethylsiloxane 100000 cP 4.6%, polydimethylsiloxane 20000 9%, silanized fumed silica 4%, micronized quartz 13%, soda glass powder 35%, aluminum silicate 11.2%, platinum catalyst 0.7%.

Component B Comprises the Following:
polydimethylsiloxane 200 cP 4%, polydimethylsiloxane 2000 cP 8.2%, polydimethylsiloxane 20000 6.4%, reticulating agent 8.5%, silanized fumed silica 2.85%, micronized quartz 18%, soda glass powder 42.05%, tungsten 10%

By replacing tungsten oxide of Example 7 with tungsten nothing changes, FIG. 9.

Example 9

Component A Comprises the Following:
polydimethylsiloxane 200 cP 8%, polydimethylsiloxane 2000 cP 15%, polydimethylsiloxane 100000 cP 4.2%, polydimethylsiloxane 20000 8.3%, silanized fumed silica 4%, soda glass powder 10.3%, aluminum silicate 9.5%, zirconium oxide 40%, platinum catalyst 0.7%.

Component B Comprises the Following:
polydimethylsiloxane 200 cP 4.4%, polydimethylsiloxane 2000 cP 9.3%, polydimethylsiloxane 20000 7%, reticulating agent 9.3%, silanized fumed silica 3%, soda glass powder 27%, zirconium oxide 40%

The radio-opacity level is very good, FIG. 10, which proves that too small concentrations have a scarce effect.

Example 10

The strips having different thickness of Example 9 have been X-rayed on soft tissues, bone tissues and teeth, thus obtaining a sufficient contrast so as to enable their identification. In a particular test a small triangle with a thickness of 0.2 mm could be seen on incisors and gingival tissues.

Example 11

The composition of Example 9 has undergone a traction test according to ASTM D412-98 at a traction speed of 100 mm/min, a bearing strain test and an elastic recovery test according to ISO 4823 (2000) standard compared with a commercial material for impression-taking based on polyether with a hardness 57 Shore A. The material of Example 9 has a hardness of 62 Shore A.

Figure 12:
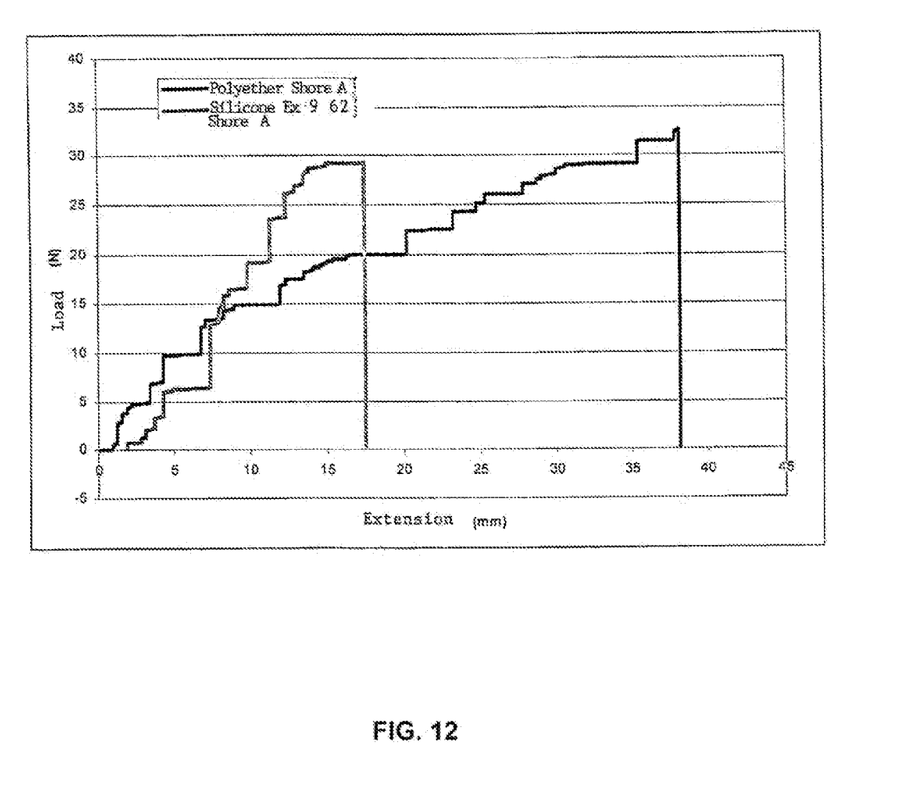
FIG. 12 shows results and data as discussed in Example 11.

The graph FIG. 12 shows the different elastic traction behavior of the two materials (polyether S57 Shore A and material as in Example 9, 62 Shore A):

The silicone of Example 9 has a tensile strength that can be compared to polyether, but a far lower extension before breaking. This-means a lower tendency to yielding and therefore to irreversible deformations.

If said behavior is accompanied by an elastic recovery of 98.6% and a bearing strain of 2.5 versus, respectively, 96.9% and 5.6% of polyether, it can be inferred that the material according to the patent certainly has a higher non-deformability to stresses generating when taking out the impression, and thus the highest accuracy in detecting the transfer and keeping it in position. FIG. 12 shows extension (mm) as a function of load (N).

Example 12

Figure 11:
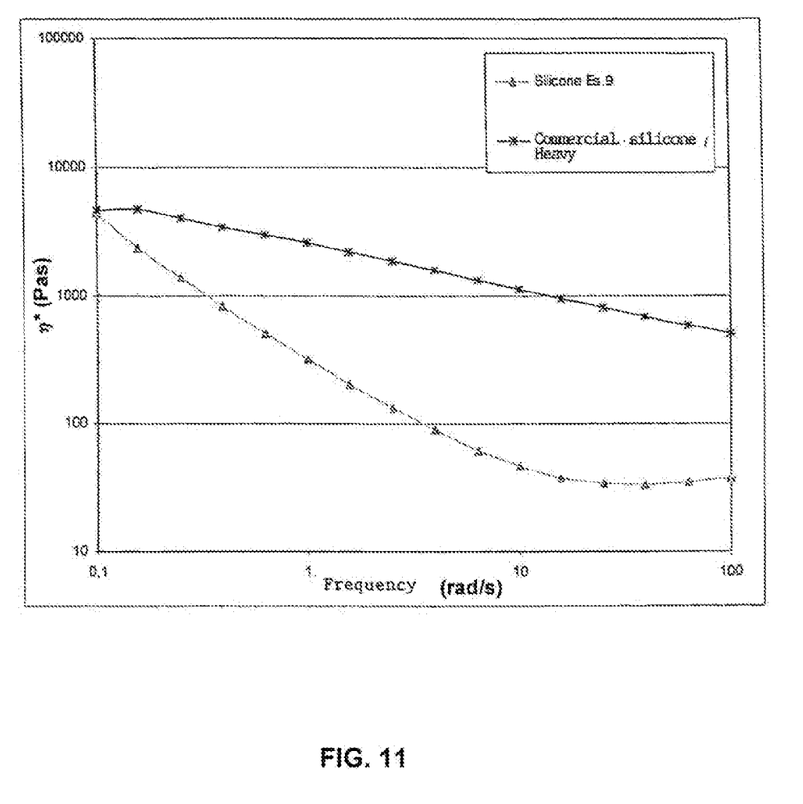
FIG. 11 shows results and data as discussed in Example 12.

Explanation of FIG. 11. FIG. 11 shows frequency (rad/seconds) as a function of viscosity (Pas): the silicone of Example 9 is compared with a commercial silicone with a frequency sweep test carried out with a controlled stress rheometer Rheomettics SR2000. Beyond the various characteristics shown in Example 11, the formulations should also optimize the rheologic features so as to simplify its extrusion from the cartridges and to optimize viscosity during impression-taking.

Example 13

Figure 13:
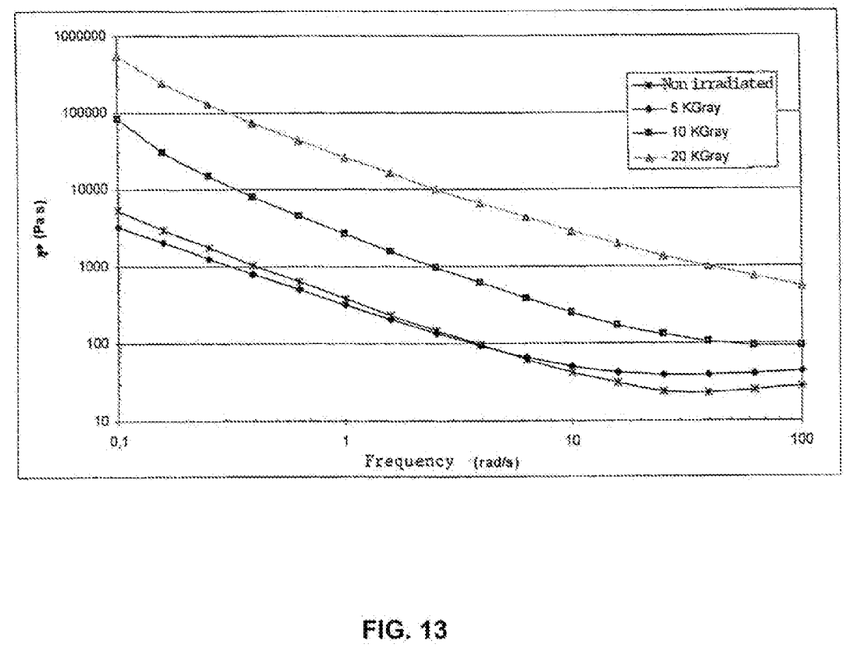
FIG. 13 shows results and data as discussed in Example 13.

Composition B of Example 9 has undergone a gamma radiation resistance test. The samples have been exposed to an irradiation with gamma radiations of 5, 10 and 20 kGray. It is related that a dose of 1.5 to 4.5 kGray kills most pathogenic bacteria except for spores. FIG. 13 shows the effect of radiations on the viscosity of component B. FIG. 13 shows frequency (rad/seconds) as a function of viscosity (Pas) of a non-irradiated sample, a sample irradiated at 5 kGray, 10 Kgray and 20 kGray. Viscosity curves have been obtained with a controlled stress rheometer Rheometrics SR2000. Irradiation dose should take into consideration degradation effects on the product.

Example 14

A composition like the one in Example 9 has undergone a temperature sterilization resistance test at 121° C. for 30 minutes. The total working-time and the setting time before and after the sterilization treatment have been checked at 35° C. with a cycloviscograph Brabender following the indications provided for in ISO 4823 standard.

The values of total working time and setting time, respectively one minute and twenty-four seconds and two minutes and thirty seconds before treatment, were unchanged.

The invention claimed is:

1. A method for impression-taking in immediate loading technique in a patient's mouth that contains an open wound, comprising the steps of:
   i) providing a radiopaque and aseptic material comprising a first component A and a second component B; said components A and B are selected from the group consisting of diorganopolysiloxane polymers having the following formula (I):

where $R^1$ and $R^2$ are an un-substituted monovalent hydrocarbon radical; the integer m is such that the viscosity of the polymer at 23° C. is comprised from 50 cP to 1,000,000 cP, wherein said material further comprises an insoluble radio-opacifying filler,
   ii) applying said material to a site in the patient's mouth and forming an impression of said mouth with said material,
   iii) removing said impression containing material from said mouth; and
   iv) inspecting the patient's mouth for any residual said radiopaque material to be removed, wherein the step of inspecting comprises use of radiography about 10 days after said removing step.

2. The method according to claim 1, in which the insoluble radio-opacifying filler is selected from the group consisting of:
finely divided metals: zinc, tungsten, silver, ytterbium, yttrium, gadolinium, zirconium, strontium, tantalum, niobium, molybdenum and lanthanum
finely divided alloys of the aforesaid metals: zinc, tungsten, silver, ytterbium, yttrium, gadolinium, zirconium, strontium, tantalum, niobium, molybdenum and lanthanum;
finely divided oxides of the aforesaid metals: zinc, tungsten, silver, ytterbium, yttrium, gadolinium, zirconium, strontium, tantalum, niobium, molybdenum and lanthanum; yttrium oxide, bismuth oxide, ytterbium oxide, tungsten oxide, niobium oxide, tantalum oxide, molybdenum oxide, zirconium oxide;
finely divided sulfates of the aforesaid metals: zinc, tungsten, silver, ytterbium, yttrium, gadolinium, zirconium, strontium, tantalum, niobium, molybdenum and lanthanum; barium sulfate and strontium sulfate;
finely divided carbonates of the aforesaid metals: zinc, tungsten, silver, ytterbium, yttrium, gadolinium, zirconium, strontium, tantalum, niobium, molybdenum and lanthanum, bismuth oxycarbonate, strontium carbonate;
and other compounds selected from the group consisting of bismuth oxychloride, calcium tungstate, tungsten carbide, wolfram carbide, molybdenum carbide, niobium carbide, tantalum carbide and zirconium carbide.

3. The method according to claim 1, in which the groups $R^1$ and $R^2$ are selected from the group consisting of: methyl, ethyl, phenyl and vinyl.

4. The method according to claim 3, in which the groups $R^1$ and $R^2$ are methyl.

5. The method according to claim 1, in which integer m is such that the viscosity of the polymer at 23° C. is comprised from 200 to 100,000 cP.

6. The method according to claim 1, in which said material further comprises silicone oils as plasticizers.

7. The method according to claim 1, in which component A further comprises a hydrosilylation catalyst.

8. The method according to claim 1, in which component B further comprises a reticulating agent.

9. The method according to claim 1, in which said material further comprises a filler chosen among: extending fillers with filling, sliding and appearance properties and reinforcing fillers with reinforcing function.

10. The method according to claim 9, in which extending fillers are chosen among: calcium carbonate, infusorial earth, iron oxide, aluminum silicates and alumina having a BET surface below 50 $m^2/g$.

11. The method according to claim 9, in which reinforcing fillers are chosen between: fumed silica and precipitated silica.

12. The method according to claim 1, wherein said radiopaque material is 10-70% by weight insoluble radio-opacifying filler.

13. The method according to claim 1, wherein said radiopaque material is 20-60% by weight insoluble radio-opacifying filler.

14. The method of claim 1, wherein said radiography comprises dental arch radiography or intra-oral radiography.

* * * * *

UNITED STATES PATENT AND TRADEMARK OFFICE
CERTIFICATE OF CORRECTION

PATENT NO. : 7,592,377 B2  Page 1 of 1
APPLICATION NO. : 10/799269
DATED : September 22, 2009
INVENTOR(S) : Rossi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 626 days.

Signed and Sealed this

Twenty-first Day of September, 2010

David J. Kappos
*Director of the United States Patent and Trademark Office*